United States Patent

Potthoff-Karl et al.

Patent Number: 5,306,484
Date of Patent: Apr. 26, 1994

[54] HAIR SETTING COMPOSITION

[75] Inventors: Birgit Potthoff-Karl, Weinheim; Axel Sanner, Frankenthal; Karin Sperling-Vietmeier, Neustadt, all of Fed. Rep. of Germany

[73] Assignee: BASF Aktiengesellschaft, Ludwigshafen, Fed. Rep. of Germany

[21] Appl. No.: 874,203

[22] Filed: Apr. 27, 1992

Related U.S. Application Data

[63] Continuation of Ser. No. 459,319, Dec. 29, 1989, abandoned.

[30] Foreign Application Priority Data

Jan. 18, 1989 [DE] Fed. Rep. of Germany ....... 3901325

[51] Int. Cl.$^5$ ............................ A61K 7/00; A61K 7/11
[52] U.S. Cl. ........................................ 424/47; 424/71
[58] Field of Search ............... 424/81, 71, 47, DIG. 1, 424/DIG. 2; A61K 7/11

[56] References Cited

U.S. PATENT DOCUMENTS

| 3,025,219 | 3/1962 | Maeder | 424/81 X |
| 3,726,288 | 4/1973 | Nowak et al. | 424/71 X |
| 4,122,248 | 10/1978 | Pfleger | 526/318.45 |
| 4,192,861 | 3/1980 | Micchelli | 424/71 |
| 4,578,426 | 3/1986 | Lenz | 525/123 |
| 4,588,673 | 5/1986 | Kataoka | 430/517 |
| 4,767,613 | 8/1988 | Nuber et al. | 424/71 X |

Primary Examiner—Thurman K. Page
Assistant Examiner—Sally Gardner
Attorney, Agent, or Firm—Oblon, Spivak, McClelland, Maier & Neustadt

[57] ABSTRACT

Hair setting composition containing as film formers copolymers based on tert-butyl acrylate and/or tert-butyl methacrylate, having a K value of from 10 to 50 and obtainable by free radical polymerization of A) from 75 to 99% by weight of tert-butyl acrylate and/or tert-butyl methacrylate,
B) from 1 to 25% by weight of acrylic acid and/or methacrylic acid and
C) from 0 to 10% by weight of a further free radical copolymerizable monomer, the carboxyl groups of the copolymers having been partly or wholly neutralized by amines.

10 Claims, No Drawings

HAIR SETTING COMPOSITION

This application is a continuation of application Ser. No. 07/459,319, filed on Dec. 29, 1989, now abandoned.

The present invention relates to a hair setting composition which contains as a film former a copolymer based on tert-butyl acrylate or methacrylate, having a K value of 10 to 50, and obtainable by free radical polymerization of A) from 75 to 99% by weight of tert-butyl acrylate or methacrylate as monomer A,
B) from 1 to 25% by weight of acrylic or methacrylic acid as monomer B and
C) from 0 to 10% by weight of a further free radical copolymerizable monomer C, the carboxyl groups of the copolymer having been partly or wholly neutralized by an amine.

Japanese Patent 71/27,480 relates in general to hairsprays which contain a copolymer of an unsaturated carboxylic acid and a second ethylenically unsaturated compound in an amine-neutralized form. An example mentioned therein is a terpolymer of 45% by weight of butyl acrylate, 40% by weight of methyl methacrylate and 15% by weight of acrylic acid. Tertiary butyl esters of unsaturated carboxylic acids are not mentioned as starting materials for preparing these copolymers.

U.S. Pat. No. 4,543,249 describes a copolymer of from 70 to 90% by weight of methyl methacrylate and from 10 to 30% by weight of methacrylic acid as a hairspray constituent whose carboxyl groups have been 50-100% neutralized with a water-soluble base.

British Patent 1,410,012 relates to hairsprays which contain a non-neutralized copolymer of from 10 to 90% by weight of acrylic or methacrylic acid and from 10 to 90% by weight of a $C_1$-$C_3$-alkyl acrylate or methacrylate.

Hairsprays are increasingly formulated with hydrocarbons instead of halocarbons as propellants. Prior art sprays also include, as film formers, the abovementioned copolymers of acrylic or methacrylic acid and alkyl esters thereof. These copolymers, then, even in the neutralized form, are still in some instances in need of improvement as regards compatibility with the apolar hydrocarbon components of the sprays; that is, the copolymers are not sufficiently soluble in the hydrocarbons. In addition, the hair setting effect of these copolymers still leaves something to be desired.

It is an object of the present invention to provide a film former for hair setting compositions which shows excellent compatibility with apolar propellants based on hydrocarbons and also has an excellent hair setting effect.

We have found that this object is achieved by the hair setting composition defined at the beginning.

The copolymer of the hair setting composition according to the present invention is chiefly composed of from 75 to 99% by weight, preferably from 85 to 98% by weight, of tert-butyl acrylate or methacrylate as monomer A and from 1 to 25% by weight, preferably from 2 to 15% by weight, of acrylic or methacrylic acid as monomer B. Particularly good results are obtained with a copolymer composed of from 75 to 99% by weight, preferably from 85 to 98% by weight, of tert-butyl acrylate and from 1 to 25% by weight, preferably from 2 to 15% by weight, of methacrylic acid.

If the properties of the copolymer are to be slightly modified, it may contain a further free radical copolymerizable monomer C as copolymerized units in an amount of up to 10% by weight, in particular up to 5% by weight. A suitable monomer C is for example the methyl, ethyl, n-propyl or n-butyl ester of acrylic or methacrylic acid, N-vinylpyrrolidone or vinyl acetate.

This copolymer is prepared by free radical copolymerization of monomers A and B and any C if used. The copolymerization is carried out by a conventional polymerization technique, for example as a suspension, emulsion or solution polymerization.

The solution polymerization in an organic solvent, in general an alcohol, has been found to be particularly advantageous. It is customarily carried out at from 60° to 130° C. and at atmospheric pressure or under autogenous pressure.

The initiator used for the free radical polymerization reaction is a customary peroxo or azo compound, for example dibenzoyl peroxide, tert-butyl perpivalate, tert-butyl per-2-ethylhexanoate, di-tert-butyl peroxide, tert-butyl hydroperoxide, 2,5-dimethyl-2,5-di(tert-butylperoxy)hexane or azobisisobutyronitrile, advantageously in an amount of from 0.1 to 2% by weight, based on the weight of monomers. The amounts of monomers and solvent are advantageously chosen in such a way as to produce a 30-80% strength by weight solution of the copolymer.

The copolymer should have a K value of from 10 to 50, preferably from 15 to 35. The particular desired K value can be obtained in a conventional manner through choice of the polymerization conditions, for example the polymerization time and the initiator concentration. The K value, which is a measure of molecular weight, is determined by the method of Fikentscher, Cellulosechemie, 13 (1932), 58–64, at 25° C. in a solution in ethanol.

A copolymer of this type customarily has a glass transition temperature of from 50° to 130° C., in particular from 60° to 100° C.

For use in the hair setting composition according to the present invention, the carboxyl groups of the resulting copolymer are partly or wholly, advantageously 5–100%, preferably 30–90%, neutralized with an amine, preferably with a mono-, di- or trialkanolamine of from 2 to 5 carbon atoms in the alkanol moiety which may be in etherified form, for example mono-, di- or triethanolamine, mono-, di- or tri-n-propanolamine, mono-, di- or triisopropanolamine, 2-amino-2-methylpropanol or di(2-methoxyethyl)amine, an alkanediolamine of from 2 to 5 carbon atoms, for example 2-amino-2-methyl-1, 3-propanediol or 2-amino2-ethyl-1,3-propanediol, or a primary, secondary or tertiary alkylamine of from 5 to 10 carbon atoms in total, eg. N,N-diethylpropylamine.

Particularly good results are obtained with 2-amino-2-methylpropanol, triisopropanolamine and 2-amino-2-ethyl-1,3-propanediol.

The hair setting composition according to the present invention is used for example as a hair gel, a hair mousse or especially as a hairspray. Particular preference is given to a hairspray which contains the following ingredients:

from 0.1 to 20% by weight, preferably from 0.5 to 10% by weight, in particular from 2 to 10% by weight, of the partially or completely neutralized copolymer, from 10 to 95% by weight, preferably from 20 to 60% by weight, in particular from 25 to 50% by weight, of a customary solvent such as in particular ethanol or isopropanol but also acetone, n-propanol, n-butanol, 2-methoxy-1-propanol, n-pentane, n-hexane, cyclohexane, n-heptane, n-octane or dichloromethane, or a mixture thereof, and from 5 to 90% by weight, preferably from 30 to 80% by weight, in particular from 45 to 70% by weight, of a customary propellant such as propane, n-butane, isobutane, 2,2-dimethylbutane, isopentane, dimethyl ether, fluorotrichloromethane, dichlorodifluoromethane or dichlorotetrafluoroethane, or a mixture thereof. Of the propellants mentioned, in particular the hydrocarbons, especially propane and n-butane, are used. If necessary, one or more of the chlorofluorocarbons mentioned are used in propellant mixtures, but only in small amounts, say up to 20% by weight, based on the propellant mixture.

In addition, such a spray formulation may contain a small amount of a perfume oil, for example from 0.1 to 5.0% by weight.

A standard spray formulation has for example the following composition:
- 6.3% by weight of the 75% 2-amino-2-methylpropanol neutralized copolymer,
- 33.7% by weight of ethanol
- 60.0% by weight of 40:60 w/w propane/n-butane.

The bulk of the ethanol can be replaced by another solvent, for example a hydrocarbon such as n-pentane or n-hexane, without impairing the hair setting effect. Similarly, the proportion of neutralized copolymer can be raised to 8-9% by weight. The propellant used can also be n-butane alone.

The copolymer present in the hair setting composition according to the present invention is highly compatible with the apolar propellants of sprays, in particular with hydrocarbons such as propane or n-butane or a mixture thereof. In general, it achieves a compatibility of from 70 to 85% by weight combined with a remarkable hair setting effect, as evidenced by the high curl retention values which are here normally above 90%. In addition, the hair setting composition according to the present invention is notable in that it causes very little stickiness on the hair, if any.

EXAMPLES

Example 1

Copolymer of 92% by weight of tert-butyl acrylate and 8% by weight of methacrylic acid A solution of 92 g of tert-butyl acrylate, 8 g of methacrylic acid and 1.0 g of tert-butyl perpivalate in 545 g of ethanol was heated to 75° C. After the polymerization had started, as evidenced by an increase in the viscosity, a mixture of 828 g of tert-butyl acrylate, 72 g of methacrylic acid and 88 g of ethanol and a solution of 4.9 g of tert-butyl perpivalate in 123 g of ethanol were added simultaneously over 3 hours during which 77–80° C. was maintained by gentle boiling. At the same temperature a solution of 4.9 g of tert-butyl perpivalate in 123 g of ethanol was then added dropwise in the course of a further 3 hours.

The polymer content of the solution obtained was 53% by weight. The copolymer had a K value of 22.8 (measured in a 2.0% strength by weight ethanol solution at 25° C.) and a glass transition temperature of 69° C.

Examples 2 To 7

Examples 2 to 4 (see table) concern copolymers of tert-butyl acrylate and methacrylic acid of different compositions. In Comparative Examples 5 to 7 (see table), copolymers of n-butyl methacrylate or 2-ethylhexyl acrylate and methacrylic acid are described. Copolymers 2 to 7 were prepared as described in Example 1. Properties of the copolymers The table below shows the composition, hydrocarbon compatibility and hair setting effect of these copolymers. The table also shows the stickiness of the films on the hair for each hairspray formulation.

TABLE

Composition, hydrocarbon compatibility, curl retention and stickiness of films on the hair

| | Composition [% by weight] | | | | Hydrocarbon compatability with 40:60 w/w propane/n-butane [% by weight] | Curl retention [%] | Stickiness |
|---|---|---|---|---|---|---|---|
| | tBA | BMA | EHA | MAA | | | |
| Example | | | | | | | |
| 1 | 92 | | | 8 | 80 | 94 | none |
| 2 | 87 | | | 13 | 70 | 91 | none |
| 3 | 90 | | | 10 | 71 | 92 | none |
| 4 | 95 | | | 5 | 82 | 91 | none |
| comparative examples | | | | | | | |
| 5 | | 90 | | 10 | 67 | 50 | distinct |
| 6 | | 95 | | 5 | 74 | 47 | distinct |
| 7 | | | 90 | 10 | 94 | 45 | distinct | tBA: tert-butyl acrylate
BMA: n-butyl methacrylate
EHA: 2-ethylhexyl acrylate
MAA: methacrylic acid The hydrocarbon compatibility with a 40:60 w/w propane/n-butane mixture indicates the maximum possible percentage by weight of this propellant mixture in a spray which besides ethanol as solvent contains 3% by weight of neutralized copolymer without cloudiness appearing at 0° C.

The curl retention is a measure of the hair setting effect. It is measured in a model experiment on hair curls produced by a conventional perm in hair about 15 cm in length which was then sprayed with the particular spray from 10 cm for 4 seconds. After conditioning for 5 hours at 25° C. and 90% relative humidity, the deformation of the suspended curls is determined relative to their original shape. A high value denotes a high setting effect that is, 100% indicates that the original shape is fully intact.

The curl retention and the stickiness were determined for each of the copolymers of Examples 1 to 4 and for Comparative Examples 5 to 7 using the following standard spray formulation:

6.3% by weight of copolymer neutralized to 75% with 2 amino-2-methylpropanol
33.7% by weight of ethanol
60.0% by weight of 40:60 propane/n-butane.

We claim:

1. A hair setting composition in the form of a spray consisting essentially of, as a film former, a copolymer based on t-butyl acrylate or t-butyl methacrylate or a mixture thereof, having a K value of from 10 to 50 and obtained by free radical polymerization of (A) from 75-99% by weight of t-butyl acrylate, t-butyl methacrylate or a mixture thereof as monomer (A), (B) from 1-25 wt. % of acrylic acid, methacrylic acid or a mixture thereof as monomer (B) and (C) from 0-10% by weight of a $C_1$-$C_4$-n-alkyl(meth)acrylate, the amounts of combined components (A-C) constituting 100% by weight of the copolymer, and the carboxyl groups of the copolymer having been partially or wholly neutralized by an amine, in combination with solvents and propellants for a hair spray composition.

2. A hair setting composition as claimed in claim 1, wherein the film former is composed of
A) from 85 to 90% by weight of tert-butyl acrylate, tert-butyl methacrylate or a mixture thereof as monomer A,
B) from 10 to 15% by weight of acrylic acid, methacrylic acid or a mixture thereof as monomer B and
C) from 0 to 10% by weight of a $C_1$-$C_4$-n-alkyl(meth)acrylate copolymerizable monomer C.

3. A hair setting composition as claimed in claim 1, wherein the film former is composed of
A) from 75 to 90% by weight of tert-butyl acrylate as monomer A,
B) from 10 to 25% by weight of methacrylic aci as monomer B and
C) from 0 to 10% by weight of a $C_1$-$C_4$-n-alkyl(meth)acrylate copolymerizable monomer C.

4. A hair setting composition as claimed in claim 2, wherein the film former is composed of
A) from 85 to 90% by wight of tert-butyl acrylate as monomer A,
B) from 10 to 15% by weight of methacrylic acid as monomer B and
C) from 0 to 10% by weight of a $C_1$-$C_4$-n-alkyl(meth)acrylate copolymerizable monomer C.

5. A method for fixing hair, which comprises: applying to hair the composition of claim 1 containing said copolymer as a film former.

6. A hair setting composition as claimed in claim 1, wherein said copolymerizable monomer C is the methyl, ethyl, n -propyl or n-butyl ester of acrylic acid or methacrylic acid.

7. A hair setting composition as claimed in claim 1, wherein said solvent is a member selected from the group consisting of ethanol, isopropanol, acetone, n-propanol, n-butanol, 2-methoxy-1-propanol, n-pentane, n-hexane, cyclohexane, n-heptane, n-octane and dichloromethane.

8. A hair setting composition as claimed in claim 1, wherein said propellant is a member selected from the group consisting of propane, n-butane, isobutane, 2,2-cimethylbutane, isopentane, dimethylether, fluorotrichloromethane, dichlorodifluoromethane and dichlorotetrafluoroethane.

9. The hair setting composition of claim 1, wherein said copolymer constitutes from 0.1 to 20% by weight of the composition also containing solvents and propellants.

10. A hair setting composition in the form of a spray consisting of, as a film former, a copolymer based on t-butyl acrylate or t-butyl methacrylate or a mixture thereof, having a K value of from 10 to 50 and obtained by free radical polymerization of (A) from 75-99% by weight of t-butyl acrylate, t-butyl methacrylate or a mixture thereof as monomer (A), (B) from 1-25 wt. % of acrylic acid, methacrylic acid or a mixture thereof as monomer (B) and (C) from 0-10% by weight of a $C_1$-$C_4$-n-alkyl(meth)acrylate, the amounts of combined components (A-C) constituting 100% by weight of the copolymer, and the carboxyl groups of the copolymer having been partially or wholly neutralized by an amine, in combination with solvents and propellants for a hair spray composition.

* * * * *